US007323461B2

(12) United States Patent
Juneau et al.

(10) Patent No.: US 7,323,461 B2
(45) Date of Patent: Jan. 29, 2008

(54) USE OF METHYLENE BLUE AND RELATED COMPOUNDS TO PREVENT OR REVERSE AN EXAGGERATED HEMODYNAMIC REACTION

(75) Inventors: Martin Juneau, Longueuil (CA); Jean-François Tanguay, Ville Mont-Royal (CA); Denis Brouillette, Le Gardeur (CA)

(73) Assignee: Montreal Heart Institute, Montreal, Quebec (CA)

( * ) Notice: Subject to any disclaimer, the term of this patent is extended or adjusted under 35 U.S.C. 154(b) by 382 days.

(21) Appl. No.: 10/401,819

(22) Filed: Mar. 28, 2003

(65) Prior Publication Data
US 2003/0219495 A1    Nov. 27, 2003

(30) Foreign Application Priority Data
Mar. 28, 2002    (CA) .................................. 2379211

(51) Int. Cl.
*A61K 31/5415*    (2006.01)
*A61P 39/02*    (2006.01)
(52) U.S. Cl. ............................... 514/224.8; 514/226.2; 514/823; 514/921; 514/922
(58) Field of Classification Search ............. 514/224.8, 514/823, 921, 922, 226.2
See application file for complete search history.

(56) References Cited

U.S. PATENT DOCUMENTS 5,854,240 A * 12/1998 Kupfer et al. ............ 514/224.8

OTHER PUBLICATIONS

Webster's New World Dictionary, Simon & Schuster, Inc., NY, 1988, p. 1067.*
Goldstein I., Lue TF, Padma-Nathan H., et al. Oral sildenafil in the treatment of erectile dysfunction. N Engl J Med 1998:338:1397-1404.
Webb D. J., Muirhead G. J., Wulff M., Sutton A., Levi R., and Dinsmore W. W. Sildenafil citrate potentiates the hypotensive effects of nitric oxide donor drugs in male patients with stable angina. JACC 2000;36:25-31.
Jackson, G., Benjamin N., Jackson N., and Allen M. J. Effects of sildenafil citrate on human hemodynamics. Am J Cardiol 1999;83:13C-20C.
Webb D.J., Freestone S., Allen M. J., and Muirhead G. J. Sildenafil Citrate and blood-pressure-lowering drugs: results of drug interaction studies with an organic nitrate and a calcium antagonist. Am J Cardiol 1999;83:21C-28C.
Yoo K. Y., Kim H. S., Moon J. -D., and Lee J. Sildenafil (Viagra®) augments sodium nitroprusside-induced but not nitroglycerin-induced hypotension in dogs. Anesth Analg 2002;94:1505-9.
Schalcher C., Schad K., Brunner-La Rocca H. P., Schindler R., Oechslin E., Scharf C., Suetsch G., Bertel O., Kiowski W. Interaction of sildenafil with cAMP-mediated vasodilation in vivo. Hypertension. 2002;40:763-7.

Ishikura, F., Beppu S., Hamada T., Khandheria B. K., Seward J. B., and Nehra A., Effects of sildenafil citrate (Viagra) combined with nitrate on the heart. Circulation. 2000;102:2516-2521.
Kleinsasser A., Loeckinger A., Hoermann C., Puehringer F. Mutz N., Bartsch G., and Lindner K. H., Sildenafil modulates hemodynamics and pulmonary gas exchange. Am J Respir Crit Care Med 2001;163:339-343.
Herrmann H. C., Chang G., Klughertz B. D., and Mahoney P. D. Hemodynamic effects of sildenafil in men with severe coronary artery disease. N Engl J Med 2000;342:1622-6.
Pfizer Inc., Customer Advocacy Medical Information, date unavailable.
Cheitlin, M.D., Hutter, A. M., Brindis, R. G., Ganz, P., Kaul S., Russell, R. O., and Zusman, R. M. Use of sildenafil (Viagra) in patients with cardiovascular disease. Circulation. 1999;99:168-177.
Memis D., Karamanlioglu B., Yuksel M., Gemlik I., and Pamukcu Z., The influence of methylene blue infusion on cytokine levels during severe sepsis. Anaesth Intensive Care 2002; 30(6) : 755-62. (one page).
Koelzow H., Gedney J. A., Baumann J., Snook N. J. and Bellamy M. C., The effect of methylene blue on the hemodynamic changes during ischemia reperfusion injury in orthotopic liver transplantation. Anesth Analg 2002; 94; 824-9.
Ishizuka N et al.: "Hypotensive interaction of sildenafil and nicorandil in rats through the cGMP pathway but not by K(ATP) channel activation," Japanese Journal of Pharmacology 2000 Japan, vol. 84, No. 3, 2000, pp. 316-324.
Holzmann, S: "Cyclic GMP as possible mediator of coronary arterial relaxation by nicorandil (SG-75)." Journal of Cardiovascular Pharmacology 1983 United States, vol. 5, No. 3, 1983, pp. 364-370.
Agha A M et al: "Sildenafil inhibits agonist-evoked rat uterine contractility: influence of guanylyl cyclase inhibition." European Journal of Pharmacology 2001; 428(3) ; 343-8.
Jain N K et al: "Sildenafil—induced peripheral analgesia and activation of the nitric oxide-cyclic GMP pathway." Brain Research 2001; 909(1-2); 170-8.
Sakuma Ichiro et al: "Interactions of sildenafil with various coronary vasodilators in isolated porcine coronary artery." European Journal of Pharmacology 2002; 437(3); 155-63.
Chandran S et al: "Nitric oxide: Concepts, current perspectives and future therapeutic implications." Indian Journal of Pharmacology 1998 India; vol. 30, No. 6; 351-366.

(Continued)

*Primary Examiner*—John Pak
(74) *Attorney, Agent, or Firm*—Holland & Hart, LLP

(57) ABSTRACT

The present invention relates to the use of the dye methylene blue (MB) or a related compound to prevent or reverse an exaggerated hemodynamic reaction in animals in need thereof, including humans. More specifically, the present invention concerns the use of MB or a related compound to prevent or reverse hypotension, unstable angina, myocardial infarction or shock caused by the concomitant ingestion of a phosphodiesterase inhibitor, such as sildenafil citrate, and a NO-donor, such as L-arginine, or an organic nitrate, such as nitroglycerin.

8 Claims, 5 Drawing Sheets

OTHER PUBLICATIONS

O'Rourke M et al: "Sildenafil/Nitrate Interaction." One page.

Robert M. Wallis, PhD. Jackie D. Corbin, PhD, Sharron H. Francis, PhD, and Peter Ellis, PhD, "Tissue Distribution of Phosphodiesterase Families and the Effects of Sildenafil on Tissue Cyclic Nucleotides, Platelet Function, and the Contractile Responses of Trabeculae Carneae and Aortic Rings in Vitro," The American Journal of Cardiology, Mar. 4, 1999, 10 pages, vol. 83 (5A), Excerpta Medica Inc., Bridgewater, New Jersey.

* cited by examiner

USE OF METHYLENE BLUE AND RELATED COMPOUNDS TO PREVENT OR REVERSE AN EXAGGERATED HEMODYNAMIC REACTION

FIELD OF THE INVENTION

The present invention relates to the use of the dye methylene blue (MB) or a related compound to prevent or reverse an exaggerated hemodynamic reaction in animals in need thereof, including humans. More specifically, the present invention concerns the use of MB or a related compound to prevent or reverse hypotension, unstable angina, myocardial infarction or shock caused by the concomitant ingestion of a phosphodiesterase inhibitor, such as sildenafil citrate, and a NO-donor, such as L-arginine, or an organic nitrate, such as nitroglycerin.

BACKGROUND OF THE INVENTION

Sildenafil citrate, sold under the trade name Viagra®, has been recognized as the first effective oral treatment for erectile dysfunction (ED) of various etiologies.[1] Its mechanism of action works as follows. Under conditions of normal sexual stimulation, the penile erectile process is regulated by release of the neurotransmitter nitric oxide (NO), which in turn induces the production of cyclic guanosine monophosphate (cGMP). Increased levels of cGMP lead to relaxation of smooth muscle in the corpus cavernosum and to engorgement of the penis with blood, resulting in an erection. Sildenafil, which is a selective inhibitor of phosphodiesterase type 5 (PDE5), an enzyme that is found in high concentrations in the corpus cavernosum, reduces the metabolism of cGMP and thereby facilitates the achievement and maintenance of an erection that is satisfactory for sexual performance.[2]

Nitric Oxide is also an important regulator of cardiovascular function because it mediates tonic relaxation of vascular smooth muscle. Endothelium-bound NO synthase tightly controls the formation of NO from the amino acid L-arginine. Release of NO activates guanylate cyclase and the generation of cGMP. Once stimulated, the NO-cGMP pathway causes vasodilation of arteries and veins resulting in decreased preload and afterload. Over stimulation of the NO-cGMP pathway by administration of exogenous NO or through other mechanisms could result in significant decreases in systemic blood pressure (BP) and symptoms of hypotension.[3]

Sildenafil produces modest, transient hemodynamic effects in healthy men or those with stable ischemic heart disease not concomitantly taking nitrates or other antianginal therapies.[4] While administration of sildenafil alone causes modest reductions in BP, such reductions have been observed to be inferior to those observed after administration of therapeutic doses of nitrates used alone for the control of angina. Because sildenafil and NO-donors act at different points in the same NO-cGMP pathway and PDE5 may participate in the termination of NO-induced actions generated in blood vessels, there is likely to be significant interaction when these two types of drugs are coadministered.[5] Recent studies have confirmed that this is in fact the case.[6] Interestingly, no synergistic or additive effect was noted between sildenafil and the calcium antagonist amlodipine in patients suffering from hypertension.[7] Additionally, no adverse cardiovascular effects of oral sildenafil were detected in men with severe coronary heart disease.[8]

The cardiovascular effects of sildenafil are important because of the frequent presence of underlying cardiac disease in men with erectile dysfunction and reports indicating serious cardiac events temporally associated with the use of this drug.[9] Sildenafil is in fact contraindicated in patients who are taking organic nitrates in any form at any time.[10] Patients with ED of vascular etiology often suffer from some form of atherosclerotic cardiovascular disease such as angina. Consequently, a sizable patient population may possess risk factors that are common to both ED and angina. Among commonly used therapeutics for angina are nitroglycerin, isosorbide mononitrate, glyceryl trinitrate and sodium nitroprusside, all of which act within tissues to generate the production of NO.[11]

As stated above, sildenafil is an agent that specifically inhibits phosphodiesterase 5 (PDE5) and is thus effective in treating ED. The market release of sildenafil in the last 2-3 years has brought to light the possibility of a dangerous interaction between sildenafil and organic nitrates. In effect, the concomitant use of sildenafil and an organic nitrate could result in a precipitous drop in blood pressure, with hypotension symptoms ranging from dizziness or light-headedness, to syncope, to a significant lowering of coronary perfusion and conversion of an area of myocardial ischemia, to infarction, with all of its potential consequences.[12] As a result of this possibility, sildenafil should not be used concurrently by patients taking an organic nitrate medication. It has been recommended that at least 24 hours should separate the use of sildenafil and the administration of an organic nitrate.[13]

According to the FDA, dozens of deaths have been reported since 1998 due to the interaction of compounds of these types. In cases where sildenafil and an organic nitrate are inadvertently taken within 24 hours of each, non-specific treatments have been recommended, such as providing aggressive fluid resuscitation or an intravenous α-adrenergic agonist such as phenylephrine.[14] There is therefore a need for an effective method or medicament to counteract the hypotensive effects of the combination of a compound such as sildenafil and an organic nitrate.

SUMMARY OF THE INVENTION

The dye methylene blue (MB) has been used as a vasoconstrictor in sepsis[15] and acute liver failure. When these conditions are associated with low mean arterial blood pressure (MAP), administration of MB increases MAP by an increase in systemic vascular resistance (SVR) and in some cases cardiac index (CI). Sepsis and ischemia reperfusion syndrome (IRS) display hemodynamic and biochemical similarities. In sepsis, these changes are associated with excess nitric oxide (NO) production. MB is believed to act by inhibiting NO synthase, reducing NO production, and by inhibiting guanylate cyclase, the target enzyme for NO.[16]

The present invention relates to the use of the dye methylene blue (MB) or a related compound to prevent or reverse an exaggerated hemodynamic reaction in animals in need thereof, including humans. Such an exaggerated hemodynamic reaction may be characterized by hypotension, unstable angina, myocardial infarction or shock. In a specific embodiment, the present invention concerns the use of MB or a related compound to prevent or reverse hypotension caused by the concomitant ingestion of a phosphodiesterase inhibitor, such as sildenafil citrate (Viagra®), vardenafil (Levitra®) or tadalafil (Cialis®), that may be used for ED, among other indications, and a NO-donor, such as L-arginine, or an organic nitrate, such as nitroglycerin, that is commonly used as a therapeutic agent for angina pectoris. It has been noted that patients already taking a hypotensive medication are at particular risk of cardiovascular collapsus when sildenafil (or another phosphodiesterase inhibitor) is ingested. Although MB has been used for a number of medical purposes, such as to effect hemodynamic changes during orthotopic liver transplantation and severe sepsis[17], to the knowledge of the inventors of the invention described herein this is the first time that the use of MB has been shown to counteract the additive effects of a compound such as sildenafil citrate and an organic nitrate.

The scope of the present invention is intended to include sildenafil citrate (Viagra®) and other molecules that inhibit phosphodiesterases with the result that the effect of NO in the body is prolonged. Compounds that are known to behave in this way include vardenafil (Levitra®) and tadalafil (Cialis®).

Similarly, the scope of the present invention is intended to encompass NO-donors, such as L-arginine, and organic nitrates such as nitroglycerin, isosorbide mononitrate, isosorbide dinitrate, pentaerythritol tetranitrate, erythrityl tetranitrate, isosorbide dinitrate/phenobarbital, glyceryl trinitrate and sodium nitroprusside, as well as illicit substances containing nitrates, such as amyl nitrite, butyl nitrate and nitrite (sometimes known as "poppers"), all of which are vasodilators.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the appended drawings.

The drops in pressure that may be observed in all of the curves result from injections of nitroglycerin. Where designated, occlusions were created in the coronary artery with a balloon catheter.

DETAILED DESCRIPTION OF THE INVENTION

Definitions

Unless defined otherwise, all technical and scientific terms used herein have the same meaning as commonly understood by one of ordinary skill in the art to which this invention belongs.

The term "analog" means a substance or compound which is chemically or structurally similar to a given substance or compound and has a biological effect which is also similar to that which the given substance or compound has or is believed to have.

The expression "concomitant ingestion" or "concomitant use" means administration of a phosphodiesterase inhibitor (such as sildenafil) followed by the ingestion of a NO-donor or organic nitrate, or vice versa, within approximately 24 hours or more (for example, 36 hours or 48 hours). The approximate time period between the use of each type of medicament specified above (for example, 24 hours) will depend on the duration of the action of the NO-donor or organic nitrate within the body.

The expression "Methylene Blue (MB) or a related compound" refers to a phenothiazine dye of the following type: 3,7-bis(dimethylamino)phenothiazin-5-ium chloride (Methylene Blue), 1,9-dimethyl-3,7-bis(dimethylamino)phenothiazin-5-ium chloride (1,9-dimethylmethylene blue). It may also include analogs of these compounds, such as, for example, 1,9-dimethyl-3-diethylamino-7-dibutylaminophenothiazine and 1,9-dimethyl-3-dimethylamino-7-diethylaminophenothiazine.

The term "prodrug" indicates a therapeutic agent that is prepared in an inactive form that is converted to an active form (i.e., the drug) within the body or cells thereof by the action of endogenous enzymes or other chemicals and/or conditions.

Other biochemistry and chemistry terms herein are used according to conventional usage in the art, as exemplified by The McGraw-Hill Dictionary of Chemical Terms (ed. Parker, S., 1985), McGraw-Hill, San Francisco).

DESCRIPTION OF EMBODIMENTS

The present invention relates to a method for preventing or reversing an exaggerated hemodynamic reaction in animals, including humans, comprising the administration of methylene blue (MB). MB, a known vasoconstrictor which inhibits guanylate cyclase, has been shown to counter the hypotension caused by the concomitant ingestion of a compound, such as sildenafil citrate (Viagra®), and an organic nitrate, such as nitroglycerin.

Figure 5:
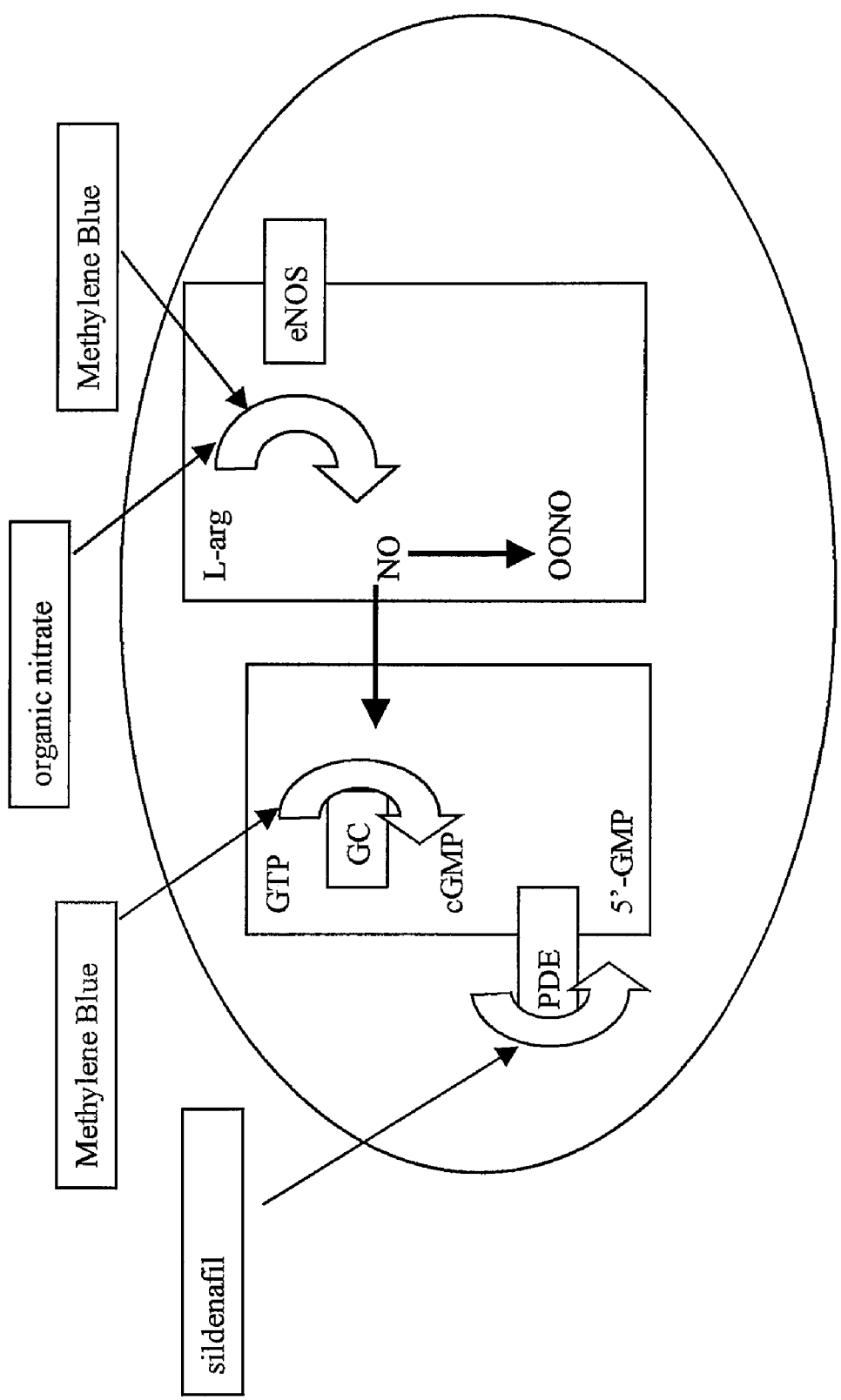
FIG. 5 The diagram, in a schematic view, illustrates metabolic pathways hypothesized to be involved in an embodiment of the present invention.

FIG. 5 shows the enzymes and mechanisms of action that are believed to be involved in the present invention. Sildenafil inhibits the phosphodiesterase that is responsible for the elimination of cGMP, which is induced by NO. The overall effectiveness of NO is thus augmented. MB, in turn, acts by inhibiting the guanylate cyclase that is linked to the formation of cGMP, thus preventing NO from exerting its effect on this guanylate cyclase. MB is also believed to have an inhibitory effect on NO synthase, thereby preventing the formation of NO. In these ways, MB exerts an overall effect that is the opposite of that resulting from sildenafil. Methylene Blue organic nitrate Methylene Blue sildenafil.

The present invention thus relates to the use of MB to prevent or reverse an exaggerated hemodynamic reaction in a mammal caused by the concomitant administration of an agent that inhibits a phosphodiesterase and a NO-donor or an organic nitrate. This hemodynamic reaction will be characterized by hypotension, unstable angina, myocardial infarction or shock, and it is therefore potentially fatal.

In an embodiment of the present invention, the organic nitrate is selected from the group consisting of: nitroglycerin, isosorbide mononitrate, isosorbide dinitrate, pentaerythritol tetranitrate, erythrityl tetranitrate, isosorbide dinitrate/phenobarbital, glyceryl trinitrate and sodium nitroprusside.

In another embodiment of the present invention, the agent that inhibits a phosphodiesterase is selected from the group consisting of: sildenafil citrate, vardenafil and tadalafil.

In yet another embodiment, the organic nitrate is selected from the group consisting of nitroglycerin, isosorbide mononitrate, isosorbide dinitrate, pentaerythritol tetranitrate, erythrityl tetranitrate, isosorbide dinitrate/phenobarbital, glyceryl trinitrate and sodium nitroprusside and the agent that inhibits a phosphodiesterase is selected from the group consisting of: sildenafil citrate, vardenafil and tadalafil.

In a specific embodiment of the present invention, the agent that inhibits a phosphodiesterase is sildenafil citrate. In another specific embodiment of the present invention, the organic nitrate is nitroglycerin. In a most specific embodiment, the agent that inhibits a phosphodiesterase is sildenafil citrate and the organic nitrate is nitroglycerin.

The present invention is intended for use on animals with cardiovascular systems, including humans.

In the present invention, MB or a related compound may be administered in a number of ways depending upon whether local or systemic treatment is desired and upon the area to be treated. Administration may be topical (for prophylactic purposes, for example), oral (in the case of a prodrug) or parenteral. Parenteral administration includes intravenous, intraarterial, subcutaneous, intraperitoneal or intramuscular injection or infusion; or intracranial, e.g., intrathecal or intraventricular, administration. Generally, the amount administered will be empirically determined, typically in the range of about 100 to 5000 μg/kg of the recipient. (Studies have shown that dosages above 2 mg/kg can lead to respiratory problems in humans.) Other additives may be included, such as stabilizers or excipients. These additives will be present in conventional amounts. The frequency of administration will also be determined empirically, depending on the severity of the condition of the animal or individual. For example, in some cases, repeat dosages may be required every few hours for 1-3 days.

While the present invention is described in terms of the use of MB or a related compound, it is believed that other compounds, namely Nitric Oxide Synthase (NOS) inhibitors as well as guanylate cyclase inhibitors, would also be effective in preventing or reversing an exaggerated hemodynamic reaction caused by the concomitant ingestion of an agent that inhibits a phosphodiesterase and a NO-donor or an organic nitrate. Possible NOS inhibitors include S-methyl-L-thiocitrulline dihydrochloride, $N^G$-Nitro-L-arginine, $N^G$-Nitro-L-arginine methyl ester (L-NAME), $N^G$-monomethyl-L-arginine monoacetate (L-NMMA), $N^G$-Nitro-L-arginineacetate, 1-(2Trifluoromethylphenyl)imidazole and 7-nitroindazole. Possible guanylate cyclase inhibitors include 6-anilino-5,8-quinolinedione (LY83583) and 1H-[1,2,4]oxadiazolo[4,3-a]quinoxalin-1-one.

To gain a better understanding of the invention described herein, the following examples are set forth. It should be understood that these examples are for illustrative purposes only. Therefore, they should not limit the scope of this invention in any way.

EXAMPLE 1

Hemodynamic Effects of Methylene Blue on Hypotensive Pigs

Materials and Methods

Pigs weighing between 20 and 25 kg were anesthetized in accordance with the standard procedure of the Canadian Council on Animal Care Regulations. After baseline hemodynamic measurements, the left circumflex (LCX) artery was occluded using a catheter balloon so as to mimic the condition of patients with cardiovascular disease. As soon as the animal was stable, a bolus injection of nitroglycerin (0.2 mg) was given intravenously in order to observe the effect of nitroglycerin alone on the animal. The animal's blood pressure was allowed to return to normal, and the animal was given 100 mg of sildenafil citrate via an esophagus tube. One hour after the administration of sildenafil citrate, a bolus injection of 0.2 mg of nitroglycerin was given to the animal in order to observe the combined effect of sildenafil nitrate and nitroglycerin on the animal. When the animal's blood pressure returned to normal, a second 0.2 mg bolus injection of nitroglycerin was given along with a bolus of MB (3 mg/kg). Blood pressure and heart rate were monitored throughout the procedure.

Results

The results demonstrate the effectiveness of MB in increasing the blood pressure in pigs whose LCX arteries were artificially occluded (in order to simulate the situation in individuals with a pre-existing cardiac condition) and which were given a combination of sildenafil and nitroglycerin within a short time of each other.

EXAMPLE 2

Hemodynamic Effects of Methylene Blue on Hypotensive Dogs

Materials and Methods

The procedure used was the same as that for pigs. (See EXAMPLE 1, above.) The experiments were conducted on dogs to see what effect the combination of a phosphodiesterase inhibitor and an organic nitrate would have on an animal with a greater number of collaterals than the pig. Since coronary arteries are end vessels, collaterals provide the alternative circulatory pathway when stenoses are present. As a result, some animals, including humans, have a larger number of collaterals than others.

Results

Figure 1:
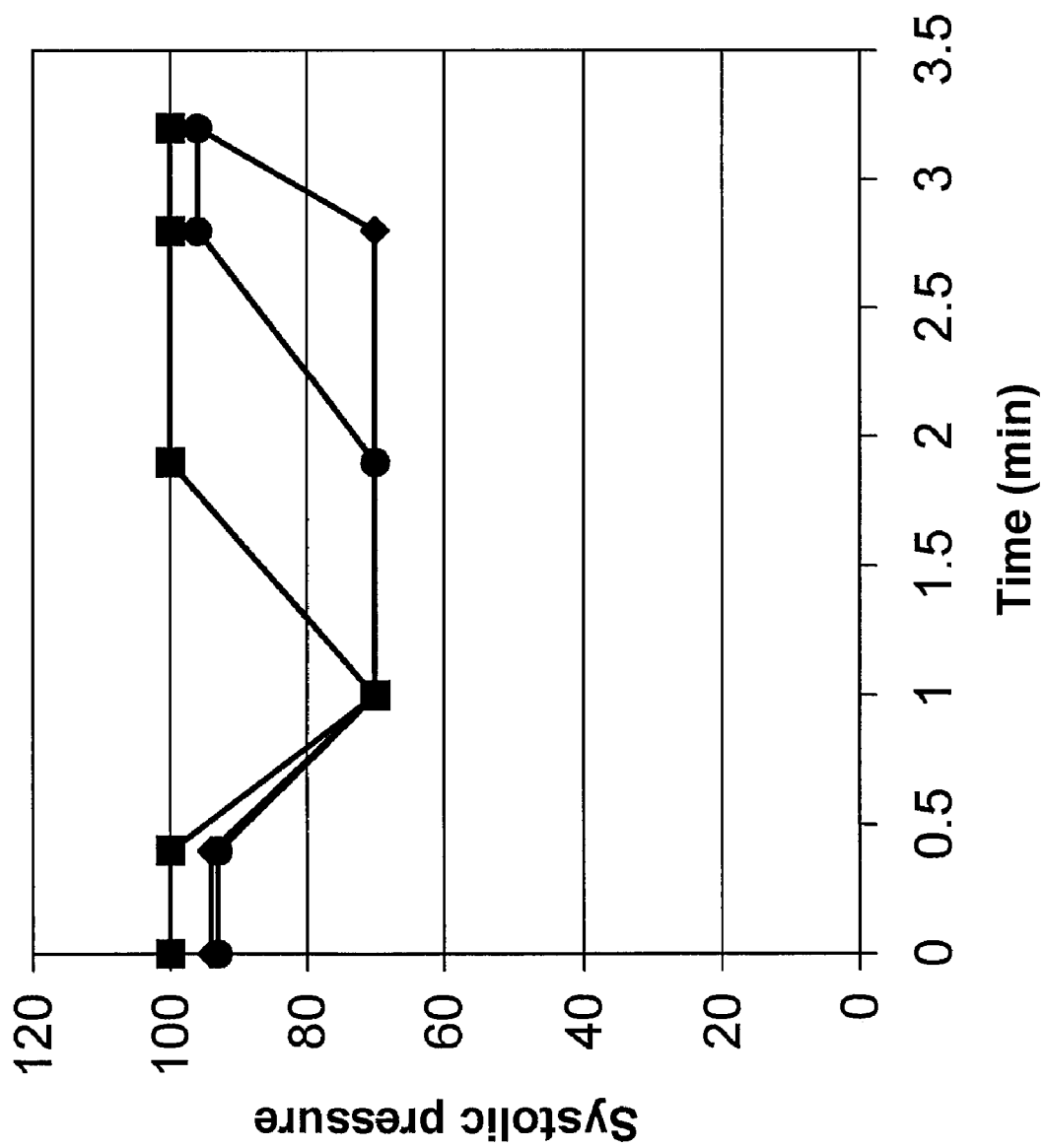
FIG. 1: The curves represent changes in time in systolic blood pressure when nitroglycerin was injected in a pig, identified as Pig #12. The curve with squares represents the systolic blood pressure with a balloon occlusion in the coronary artery. The curve with diamonds shows the effect of nitroglycerin added to a pill of sildenafil citrate. It may be observed that pressure remains low as compared with the first curve. The last curve (curve with circles) shows the beneficial effect on pressure when MB is injected in the animal. Pressure recovery was much more rapid in the presence of MB.
Figure 2:
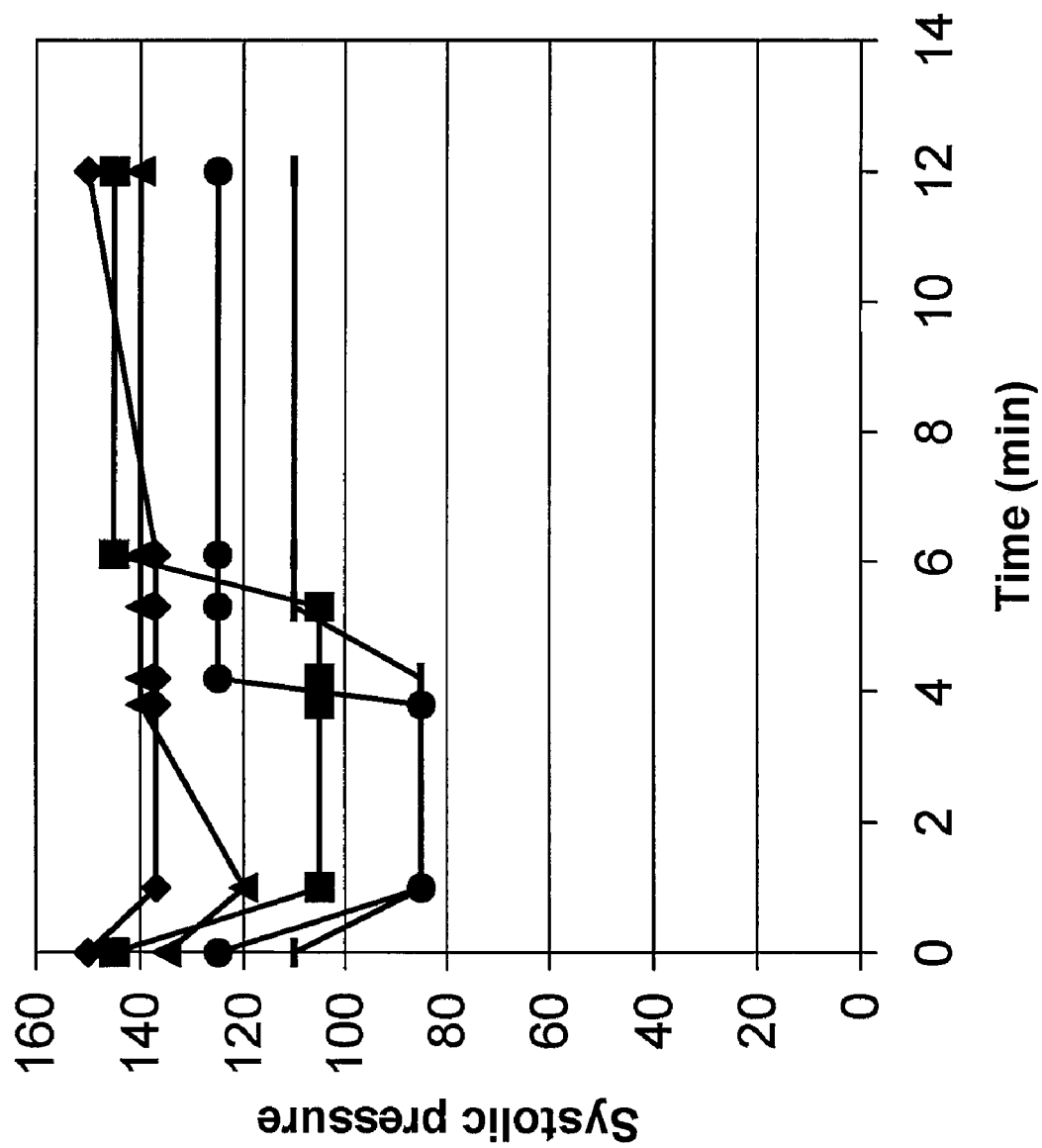
FIG. 2: The same experiment as described in respect of FIG. 1 was repeated using a second pig, identified as Pig #13. The beneficial effects of MB may be seen in the curve with circles when compared with the plain curve.
Figure 3:
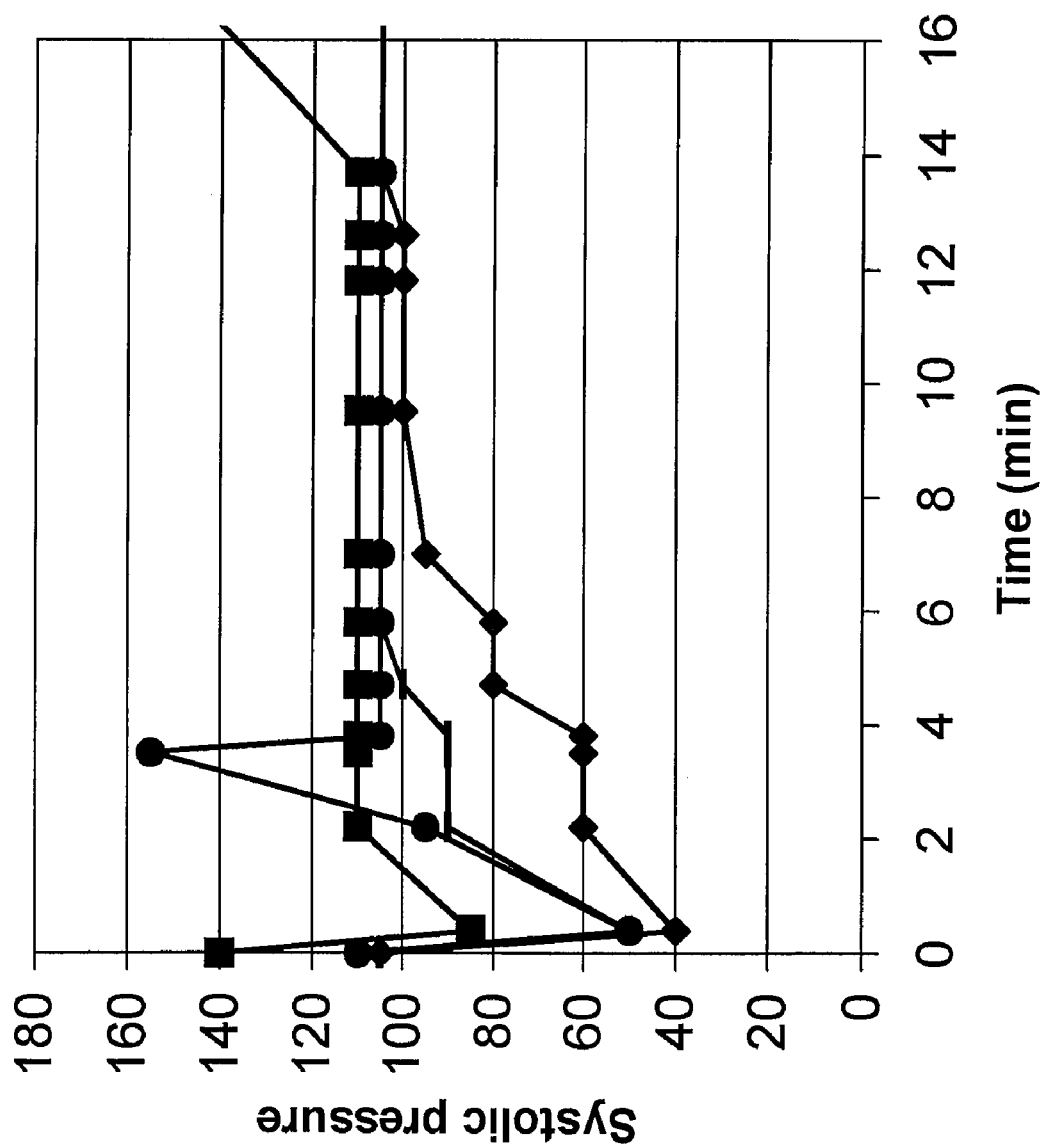
FIG. 3: The curves represent changes in time in systolic blood pressure when nitroglycerin was injected in a dog, identified as Dog #16. The plain curve and the curve with circles show the effect of MB on the pressure. A drop in blood pressure is less pronounced, and there is more rapid recovery time, than without MB (curve with diamonds).
Figure 4:
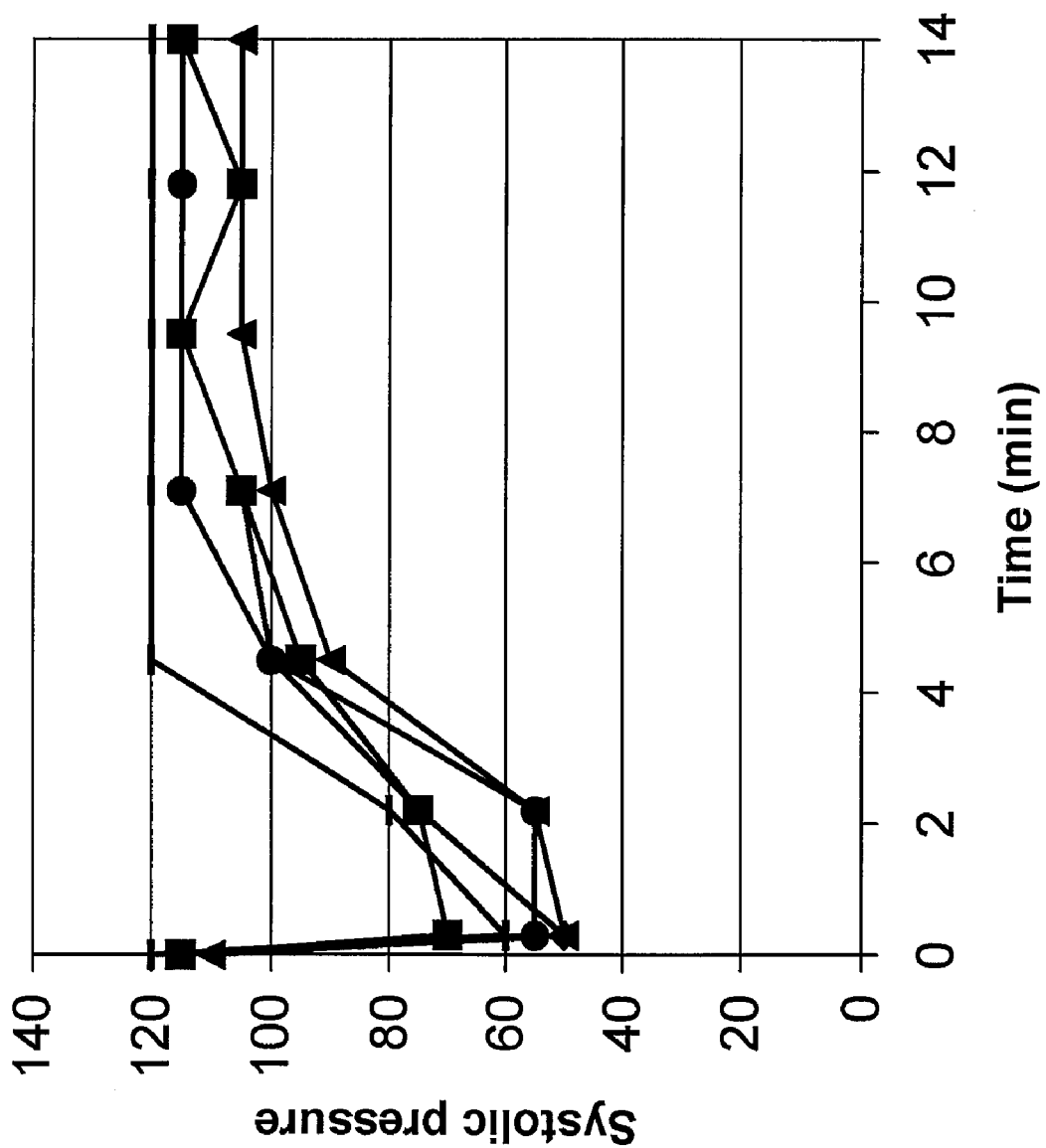
FIG. 4: The curves represent changes in time in systolic blood pressure when nitroglycerin was injected in a dog, identified as Dog #17. The plain curve and the curve with circles show the effect of MB on the pressure. A drop in pressure is less pronounced, and there is more rapid recovery time, than without MB (curve with diamonds).

While the results with this dog model are perhaps less dramatic than those from the experiments with pigs (as demonstrated by comparing FIGS. 3 and 4 with FIGS. 1 and 2), they nevertheless show the effectiveness of MB in reversing the reduction in blood pressure created by the combined administration of sildenafil and nitroglycerin. MB effectively increased the blood pressure in the animals tested.

Discussion

The results of the experiments conducted with pigs and with dogs demonstrate in two animal models the efficacy of MB in reversing drops in blood pressure (hypotension) that are caused by the combined administration of sildenafil citrate and nitroglycerin. Such drops in pressure, which in humans might occur through the inadvertent concomitant use of an organic nitrate (such as nitroglycerin) along with a phosphodiesterase inhibitor which has been taken, for example, for ED, are potentially deadly. Using MB to counteract the effects of such an exaggerated hemodynamic reaction provides a less expensive, easier-to-administer alternative to the remedies that are currently suggested in the literature.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

REFERENCES

1. Goldstein H., Lue T F, Padma-Nathan H., et al. Oral sildenafil in the treatment of erectile dysfunction. N Engl J Med 1998;338:1397-404.
2. Webb D. J., Muirhead G. J., Wulff M., Sutton A., Levi R., and Dinsmore W. W. Sildenafil citrate potentiates the hypotensive effects of nitric oxide donor drugs in male patients with stable angina. JACC 2000;36:25-31.
3. Ibid
4. Jackson, G., Benjamin N., Jackson N., and Allen M. J. Effects of sildenafil citrate on human hemodynamics. Am J Cardiol 1999;83:13C-20C.
5. Webb D. J., Muirhead G. J., Wulff M., Sutton A., Levi R., and Dinsmore W. W. Sildenafil citrate potentiates the hypotensive effects of nitric oxide donor drugs in male patients with stable angina. JACC 2000;36:25-31.
6. Webb D. J., Freestone S., Allen M. J., and Muirhead G. J. Sildenafil Citrate and blood-pressure-lowering drugs: results of drug interaction studies with an organic nitrate and a calcium antagonist. Am J Cardiol 1999;83:21C-28C; Yoo K. Y., Kim H. S., Moon J.-D., and Lee J. Sildenafil (Viagra®) augments sodium nitroprusside-induced but not nitroglycerin-induced hypotension in dogs. Anesth Analg 2002;94:1505-9; Schalcher C., Schad K., Brunner-La Rocca H. P., Schindler R., Oechslin E., Scharf C., Suetsch G., Bertel O., Kiowski W. Interaction of sildenafil with cAMP-mediated vasodilation in vivo. *Hypertension.* 2002;40:763-7; Ishikura, F., Beppu S., Hamada T., Khandheria B. K., Seward J. B., and Hehra A., Effects of sildenafil citrate (Viagra) combined with nitrate on the heart. *Circulation.* 2000;102:2516-2521; Kleinsasser A., Loeckinger A., Hoermann C., Puehringer F. Mutz N., Bartsch G., and Lindner K. H., Sildenafil modulates hemodynamics and pulmonary gas exchange. Am J Respir Crit Care Med 2001;163:339-343.
7. Webb D. J., Freestone S., Allen M. J., and Muirhead G. J. Sildenafil Citrate and blood-pressure-lowering drugs: results of drug interaction studies with an organic nitrate and a calcium antagonist. Am J Cardiol 1999;83:21C-28C.
8. Herrmann H. C., Chang G., Klugherz B. D., and Mahoney P. D. Hemodynamic effects of sildenafil in men with severe coronary artery disease. N Engl J Med 2000;342:1622-6.
9. Herrmann H. C., Chang G., Klugherz B. D., and Mahoney P. D. Hemodynamic effects of sildenafil in men with severe coronary artery disease. N Engl J Med 2000;342:1622-6.
10. Pfizer Inc., Customer Advocacy Medical Information
11. Webb D. J., Muirhead G. J., Wulff M., Sutton A., Levi R., and Dinsmore W. W. Sildenafil citrate potentiates the hypotensive effects of nitric oxide donor drugs in male patients with stable angina. JACC 2000;36:25-31.
12. Pfizer Inc., Customer Advocacy Medical Information
13. Cheitlin, J. S., Hutter, A. M., Brindis, R. G., Ganz, P., Kaul S., Russell, R. O., and Zusman, R. M. Use of sildenafil (Viagra) in patients with cardiovascular disease. *Circulation.* 1999;99:168-177.
14. Ibid
15. Memis D., Karamanlioglu B., Yuksel M., Gemlik I., and Pamukcu Z., The influence of methylene blue infusion on cytokine levels during severe sepsis. Anaesth Intensive Care 2002;30(6):755-62.
16. Koelzow H., Gedney J. A., Baumann J., Snook N. J., and Bellamy M. C., The effect of methylene blue on the hemodynamic changes during ischemia reperfusion injury in orthotopic liver transplantation. Anesth Analg 2002;94:824-9.
17. Memis D., Karamanlioglu B., Yuksel M., Gemlik I., and Pamukcu Z., The influence of methylene blue infusion on cytokine levels during severe sepsis. Anaesth Intensive Care 2002; 30(6): 755-62; Koelzow H., Gedney J. A., Baumann J., Snook N. J., and Bellamy M. C., The effect of methylene blue on the hemodynamic changes during ischemia reperfusion injury in orthotopic liver transplantation. Anesth Analg 2002;94:824-9.

What is claimed is:

1. A method of reversing an exaggerated hemodynamic reaction in a human caused by the concomitant administration of an agent that specifically inhibits a phosphodiesterase and a NO-donor or an organic nitrate, said method comprising administering methylene blue to said human in an amount therapeutically effective for reversing, at least in part, said exaggerated hemodynamic reaction.

2. A method as described in claim 1, wherein said exaggerated hemodynamic reaction is characterized by hypotension, unstable angina, myocardial infarction or shock.

3. A method as described in claim 2, wherein said agent that specifically inhibits a phosphodiesterase is selected from the group consisting of: sildenafil citrate, vardenafil and tadalafil.

4. A method as described in claim 2, wherein said NO-donor or organic nitrate is selected from the group consisting of: L-arginine, nitroglycerin, isosorbide mononitrate, isosorbide dinitrate, pentaerythritol tetranitrate, erythrityl tetranitrate, isosorbide dinitrate/phenobarbital, sodium nitroprusside, amyl nitrate, butyl nitrite nitrite and butyl nitrite.

5. A method as described in claim 2, wherein said agent that specifically inhibits a phosphodiesterase is selected from the group consisting of sildenafil citrate, vardenafil and tadalafil and said NO-donor or organic nitrate is selected from the group consisting of L-arginine, nitroglycerin, isosorbide mononitrate, isosorbide dinitrate, pentaerythritol tetranitrate, erythrityl tetranitrate, isosorbide dinitrate/phenobarbital, sodium nitroprusside, amyl nitrite nitrite, butyl nitrate and butyl nitrite.

6. A method as described in claim 5, wherein said agent that specifically inhibits a phosphodiesterase is sildenafil citrate.

7. A method as described in claim 5, wherein said organic nitrate is nitroglycerin.

8. A method as described in claim 5, wherein said agent that specifically inhibits a phosphodiesterase is sildenafil citrate and said organic nitrate is nitroglycerin.

* * * * *

UNITED STATES PATENT AND TRADEMARK OFFICE
CERTIFICATE OF CORRECTION

PATENT NO. : 7,323,461 B2
APPLICATION NO. : 10/401819
DATED : January 29, 2008
INVENTOR(S) : Martin Juneau, Jean-Francois Tanguay and Denis Brouillette It is certified that error appears in the above-identified patent and that said Letters Patent is hereby corrected as shown below:

Column 8, Line 31, "phosphodiesterase" should be deleted.

Column 8, Line 47, "amyl nitrate" should read --amyl nitrite--.

Column 8, Line 47, "butyl nitrite nitrite" should read --butyl nitrite--.

Column 8, Line 47, "butyl nitrite" should read --butyl nitrate--.

Column 8, Line 55, "amyl nitrite nitrite" should read --amyl nitrite--.

Signed and Sealed this

Nineteenth Day of August, 2008

JON W. DUDAS
*Director of the United States Patent and Trademark Office*